US009211295B2

(12) United States Patent
Ajani et al.

(10) Patent No.: US 9,211,295 B2
(45) Date of Patent: *Dec. 15, 2015

(54) 17 ALPHA, 21-DIHYDROXYPREGNENE ESTERS AS ANTIANDROGENIC AGENTS

(71) Applicant: Cassiopea S.P.A., Lainate (IT)

(72) Inventors: Mauro Ajani, Lainate (IT); Luigi Moro, Milan (IT)

(73) Assignee: CASSIOPEA S.P.A., Lainate (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/474,765

(22) Filed: Sep. 2, 2014

(65) Prior Publication Data

US 2015/0216878 A1    Aug. 6, 2015

Related U.S. Application Data

(60) Continuation of application No. 14/103,707, filed on Dec. 11, 2013, now Pat. No. 8,865,690, which is a continuation of application No. 13/398,222, filed on Feb. 16, 2012, now abandoned, which is a continuation of application No. 12/457,870, filed on Jun. 24, 2009, now Pat. No. 8,143,240, which is a division of application No. 10/486,386, filed as application No. PCT/EP02/08226 on Jul. 24, 2002, now abandoned.

(30) Foreign Application Priority Data

Aug. 10, 2001 (IT) .............................. MI2001A1762

(51) Int. Cl.
| | |
|---|---|
| A61K 31/56 | (2006.01) |
| A61K 31/573 | (2006.01) |
| C07J 5/00 | (2006.01) |
| C07J 9/00 | (2006.01) |
| A61K 9/00 | (2006.01) |
| A61K 9/127 | (2006.01) |
| A61K 47/06 | (2006.01) |
| A61K 47/10 | (2006.01) |
| A61K 47/12 | (2006.01) |
| A61K 47/14 | (2006.01) |
| A61K 47/20 | (2006.01) |

(52) U.S. Cl.
CPC ............. *A61K 31/573* (2013.01); *A61K 9/0014* (2013.01); *A61K 9/127* (2013.01); *A61K 47/06* (2013.01); *A61K 47/10* (2013.01); *A61K 47/12* (2013.01); *A61K 47/14* (2013.01); *A61K 47/20* (2013.01); *C07J 5/0053* (2013.01); *C07J 9/005* (2013.01)

(58) Field of Classification Search
USPC ........................................................ 514/178
See application file for complete search history.

(56) References Cited

U.S. PATENT DOCUMENTS

| | | | |
|---|---|---|---|
| 2,985,650 | A | 5/1961 | Batres et al. |
| 3,152,154 | A | 10/1964 | Ercoli et al. |
| 3,431,173 | A | 3/1969 | van der Waard et al. |
| 3,530,038 | A | 9/1970 | de Flines et al. |
| 3,780,177 | A | 12/1973 | Ercoli et al. |
| 4,645,763 | A | 2/1987 | Annen et al. |
| 4,670,427 | A | 6/1987 | Annen et al. |
| 5,264,428 | A | 11/1993 | Streber |

FOREIGN PATENT DOCUMENTS

| | | |
|---|---|---|
| AU | 729928 B2 | 2/2001 |
| DE | 196 53 730 A1 | 6/1998 |
| EP | 791771 | 3/1958 |
| JP | 52-10489 | 1/1977 |
| JP | 59-106500 A | 6/1984 |
| JP | 60-161998 A | 8/1985 |
| JP | 2004-530703 A | 10/2004 |
| JP | 2005-539016 A | 12/2005 |
| WO | WO 02/094843 A1 | 11/2002 |
| WO | WO 2004/014935 A1 | 2/2004 |

OTHER PUBLICATIONS

Annen, K., et al.,"17-Pivalate in der Pregnanreihe," *Liebigs Ann. Chem*:705-711, Wiley-VCH Verlag GmbH & Co. KGaA, Germany (1983).
Baldessari, A., et al., "86. Lipase-Catalysed Regioselective Deacetylation of Androstane Derivatives," Helvetica Chimica Acta 79:999-1004, Verlag Helvetica Chimica Acta, Switzerland (1996).
Belieu, R.M., "Mastodynia," *Obstetrics and Gynecology Clinics of North America* 21(3):461-477, W.B. Saunders Company, United States (1994).
Biollaz, von M. and Kalvoda, J., "263. Reaktionen von Steroiden mit Dialkylaminoschwefeltrifluoriden. I. 11β-Hydroxysteroide." *Helvetica Chimica Acta* 60(8):2703-2710, Schweizerische Chemische Gesellschaft, Switzerland (1977).
Bruttomesso, A.C. and Baldessari, A., "Lipase-catalysed deacetylation of androstane and pregnane derivatives: influence of ring D substitution," *Journal of Molecular Catalysis B: Enzymatic* 29:149-153, Elsevier B.V., Netherlands (2004).
Caira, M.R., "Crystalline Polymorphism of Organic Compounds," in *Topics in Current Chemistry*, vol. 198, de Meijere, A., et al., Eds., pp. 164-208, Springer-Verlag, Germany (1998).
Celasco, G., et al., "Biological Profile of Cortexolone 17α-Propionate (CB-03-01), a New Topical and Peripherally Selective Androgen Antagonist," *Arzneim.—Forsch./Drug Res.* 54(12):881-886, Editio Cantor Verlag, Germany (2004).
Cheung,Y.W., et al., "Resistance to enzymatic hydrolysis as a parameter in drug potency," *International Journal of Pharmaceuticals* 27:325-333, Elsevier Science Publishers B.V., Netherlands (1985).
Ferraboschi, P., et al., "Lipase-catalyzed preparation of corticosteroid 17α-esters endowed with antiandrogenic activity," *Tetrahedron Letters* 49:4610-4612, Elsevier Ltd., England (2008).

(Continued)

*Primary Examiner* — Marcos Sznaidman
(74) *Attorney, Agent, or Firm* — Sterne, Kessler, Goldstein & Fox P.L.L.C.

(57) ABSTRACT

17α,21-Dihydroxypregna-4,9(11)-diene-3,20-dione and 17α,21-dihydroxypregna-4-ene-3,20-dione 17 and/or 21 esters having remarkable antiandrogenic activity are provided, along with methods of using these compounds and processes for their preparation.

26 Claims, No Drawings

(56) References Cited

OTHER PUBLICATIONS

Ford, J.L. and Timmins, P., Eds., "Ch. 6 Thermal analysis in the characterization of pharmaceutical solids," in *Pharmaceutical Thermal Analysis: Techniques and Applications*, pp. 139-140, Ellis Horwood Limited, England (1989).

Franssen, M.C.R., et al., "Enzymatic Alcoholysis of Alkoxymethyl Alkanoates: a Possible Approach for the Kinetic Resolution of Tertiary Alcohols," *Tetrahedron Letters 39*:8345-8348, Elsevier Science Ltd., England (1998).

Gardi, R., et al., "52. Derivati di condensazione nella catena laterale di corticosteroidi.—Nota III. Preparazione e reazioni dei 17-monesteri," *Gazz. Chim. It. 93*:431-450, Palermo, Italy (1963).

Gardi, R., et al., "Corticosteroid 17α-Monoesters from 17α,21-Cyclic Orthoesters," *Tetrahedron Letters 13*:448-451, Pergamon Press Ltd., Great Britain (1961).

Hilfiker, R., Ed., "Characterization of Polymorphic Systems Using Thermal Analysis," in *Polymorphisms in the Pharmaceutical Industry*, pp. 46-48, Wiley-VCH Verlag GmbH & Co. KGaA, Germany (2006).

Meriggiola, M.C. and Pelusi, G., "Advances in male hormonal contraception," *Expert Opin. Investig. Drugs 15*(4):389-397, Ashley Publications, England (2006).

Misaki, T., et al., "Enzymic hydrolysis of hydrocortisone diesters in skin," *Yakuzaigaku 42*(2):92-98, Abstract, CAPLUS Chemical Abstract Database Accession No. 575431 (1982).

Morrison, R.T. and Boyd, R.N., Eds., "Chap. 20 Functional Derivatives of Carboxylic Acids," in *Organic Chemistry*, Sixth Edition, pp. 764-766, Prentice-Hall, Inc., Englewood Cliffs, New Jersey, United States (1992).

Schinzer, W.C., et al., "Characterization and Interconversion of Polymorphs of Premafloxacin, a New Quinolone Antibiotic," *Journal of Pharmaceutical Sciences 86*(12):1426-1431, American Chemical Society and American Pharmaceutical Association, United States (1997).

Tuladhar, M.D., et al., "Thermal behaviour and dissolution properties of phenylbutazone polymorphs," *J. Pharm. Pharmcol. 35*:208-214, Pharmaceutical Society of Great Britain, England (1983).

Turner, R.B., "Acylation of 17-Hydroxy-20-ketosteroids," *J. Am. Chem. Soc. 75*:3489-3492, American Chemical Society, United States (1953).

Voigt, W. and Hsia, S.L., "The Antiandrogenic Action of 4-Androsten-3-one-17β-Carboxylic Acid and Its Methyl Ester on Hamster Flank Organ," *Endocrinology 92*(4):1216-1222, Endocrine Society, United States (1973).

Non-Final Office Action, mailed Sep. 25, 2006 for U.S. Appl. No. 10/486,386, filed Sep. 16, 2004.

Final Office Action, mailed Apr. 13, 2007 for U.S. Appl. No. 10/486,386, filed Sep. 16, 2004.

Non-Final Office Action, mailed Sep. 7, 2007 for U.S. Appl. No. 10/486,386, filed Sep. 16, 2004.

Final Office Action, mailed Mar. 21, 2008 for U.S. Appl. No. 10/486,386, filed Sep. 16, 2004.

Non-Final Office Action, mailed Jul. 10, 2008 for U.S. Appl. No. 10/486,386, filed Sep. 16, 2004.

Final Office Action, mailed Feb. 27, 2009 for U.S. Appl. No. 10/486,386, filed Sep. 16, 2004.

Non-Final Office Action, mailed Jul. 13, 2011 for U.S. Appl. No. 12/457,870, filed Jun. 24, 2009.

Non-Final Office Action, mailed Jul. 13, 2011 for U.S. Appl. No. 14/103,707, filed Apr. 24, 2014.

17 ALPHA, 21-DIHYDROXYPREGNENE ESTERS AS ANTIANDROGENIC AGENTS

The present invention relates to 17α,21-dihydroxypregnene esters, processes for the preparation thereof and the use thereof as antiandrogenic agents.

PRIOR ART

A number of corticosteroids have been used as anti-inflammatory, anti-rheumatic, anti-allergic and anti-shock agents.

In particular, 11-deoxy-hydrocortisone esters and derivatives thereof have been widely used as anti-inflammatories.

No 17α,21-dihydroxypregnene mixed esters are known, while 17 and 21 acyl derivatives with equal aliphatic chains having no more than four carbon atoms have been described.

Carboxylic acids 17 or 21 monoesters having no more than six carbon atoms are also known.

U.S. Pat. No. 3,530,038 discloses a process for the preparation of 11β-17α-21-trihydroxy steroids which comprises subjecting 11-deoxy-17α-OR-21-OR' steroids, wherein R is a carboxylic acid residue of 1-18 carbon atoms and R' is hydrogen or an acyl of 1 to 18 carbon atoms, to microbiological oxidation with *Curvularia* for obtaining the corresponding 11β-hydroxy steroid.

U.S. Pat. No. 3,780,177 discloses the preparation of 21-hydroxy-pregna-4,9-diene-3,20-dione-17α-butanoate by means of orthobutyrates and the use thereof as an intermediate for the preparation of 6α,9α-difluoroprednisolone 17-butanoate-21 ester derivatives.

SUMMARY OF THE INVENTION

It has now been found that some 17α,21-dihydroxypregna-4,9(11)-diene-3,20-dione and 17α,21-dihydroxypregna-4-ene-3,20-dione 17 and/or 21 esters have remarkable anti androgenic activity.

Therefore, according to a first embodiment, the present invention relates to compounds of formula (I)

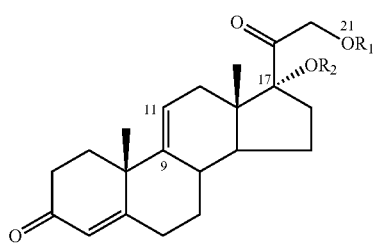

(I)

wherein:
$R_1$ and $R_2$, which can be the same or different, are hydrogen or a $C_3$-$C_{18}$ acyl group, with the provisos that:
at least one of $R_1$ and $R_2$ is different from hydrogen;
when $R_1$ is hydrogen, $R_2$ is different from butyroyl.

According to a second embodiment, the invention relates to compounds of formula (II)

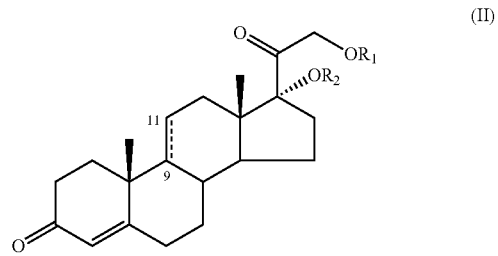

(II)

wherein:
$R_1$ and $R_2$, which can be the same or different, are hydrogen or a $C_3$-$C_{18}$ acyl group, with the proviso that:
at least one of $R_1$ and $R_2$ is different from hydrogen;
as antiandrogenic drugs.

According to a further embodiment, the invention relates to a process for the preparation of compounds of formula (I) or (II) in which $R_1$ and $R_2$ are both acyl groups, which process comprises reacting the corresponding compounds, wherein $R_1$ and $R_2$ are hydrogen, with carboxylic acids anhydrides or active esters in inert solvents and at temperatures ranging from −5° C. to the reaction mixture boiling temperature.

Still a further object of the invention relates to a process for the preparation of compounds of formula (I) or (II) wherein one of $R_1$ or $R_2$ is hydrogen and the other is acyl, which process comprises:
a. reaction of the corresponding compounds wherein $R_1$ and $R_2$ are hydrogen with $C_3$-$C_{18}$ carboxylic acids anhydrides or active esters or with allyloxycarbonyl chloride or isobutene in inert solvents and at temperatures ranging from −5° C. to the boiling temperature, for obtaining the corresponding compound in which $R_1$ is isobutyl, allyloxycarbonyl or $C_3$-$C_{18}$ acyl;
b. optional reaction of the compound from step a) with $C_3$-$C_{18}$ carboxylic acids anhydrides or active esters in inert solvents and at temperatures ranging from −5° C. to the reaction mixture boiling temperature;
c. optional lysis of the 21-allyloxycarbonyl or 21-isobutyloxy group.

Finally, the invention relates to pharmaceutical compositions with antiandrogenic activity containing as active ingredient the compounds of formula (I) or (II).

DETAILED DISCLOSURE OF THE INVENTION

Preferred compounds of formula (I) are:
17α,21-dibutanoyloxy-pregna-4,9(11)-diene-3,20-dione;
17α-hydroxy-21-butanoyloxy-pregna-4,9(11)-diene-3,20-dione;
17α-butanoyloxy-21-octadecanoyloxy-pregna-4,9(11)-diene-3,20-dione;
17α-octadecanoyloxy-21-butanoyloxy-pregna-4,9(11)-diene-3,20-dione.

The antiandrogenic activity of the compounds of formula (I) and (II) has been evaluated in the animal according to the conventional test for the topical antiandrogenic activity described by W. Voigt and S. L. Hsia (Endocrinology 1973; 92: 1216-1222).

The test was carried out on sexually immature female hamsters aged 6-8 weeks and weighing 65-90 grams.

At the beginning of the tests, the back of each animal was shaved to evidence the respective flank organ bilaterally. Animals were then subdivided into homogeneous groups and treated daily for 21 consecutive days. The tested steroids were dissolved at concentrations ranging from 100 to 400 micrograms in 50 microlitres of an acetone solution containing 4 micrograms of testosterone propionate (TP) or 4 micrograms of dihydrotestosterone (DHT). 50 Microlitres of the solutions were applied to the right flank organ, while the contralateral organ used as individual control received only acetone (50 microlitres). Control groups received TP or DHT alone, following the same procedures.

At the end of the tests, the animals were killed under ether anesthesia and the whole skin of the back was taken. The area of both flank organs was measured, separately, with transillumination. The mean differences between areas treated with the tested steroids and those treated with the carrier alone were calculated for each group, and said mean differences were compared, as inhibition percentages, to the mean differences between the areas in the control groups treated with either TP or DHT.

As shown in Examples 6 and 7, the compounds described herein inhibited by more than 80% the androgenic action of testosterone propionate (TP) and by 50 to 80% the action of its active derivative dihydrotestosterone (DHT).

The compounds of the invention proved active at doses ranging from 10 to 4000 micrograms.

The compounds of the invention can be used as suitable pharmaceutical compositions for the topical and/or systemic treatment, through the oral, cutaneous or mucosal route, of conditions such as: acne, seborrhea, hirsutism, alopecia, mastodynia, prostate hyperplasia and carcinoma, virilization syndromes in the female, early puberty, inhibition of sexual aggressiveness in the male, contraception in the male.

According to the process of the invention, compounds of formula (I) or (II) wherein $R_1$ and $R_2$ are both acyl groups are prepared by esterification of 17α,21-dihydroxypregna-4-ene-3,20-dione or 17α,21-dihydroxypregna-4,9(11)-diene-3,20-dione hydroxy groups with active esters containing the desired acyl group. According to this simple procedure, acyl derivatives with hindering aliphatic chains, such as those with high number of carbon atoms or branched, can be prepared. Examples of suitable active esters for this reaction are trifluoroethyl butyrate or trifluoroethyl octadecanoate, which can both attain excellent esterification yields with the aid of a lipase in inert anhydrous solvents at temperatures ranging from 20 to 50° C. and with reaction times ranging from 20 to 100 hours. Examples of lipases are PPL (porcine pancreatic lipase) or those from *Candida cylindracea*.

The process for the preparation of the compounds of formula (I) or (II) wherein one of $R_1$ or $R_2$ is hydrogen and the other is acyl comprises the following steps:

1. The 21 hydroxyl is selectively esterified with allyloxycarbonyl chloride, benzyloxy carbonyl chloride, tert-butyl-carbonyl chloride in dimethylformamide or isobutene at temperatures from −5 to 40° C.

2. The resulting 21 monoester is then subjected to esterification with anhydrides of carboxylic acids of 7 carbon atoms in the presence of 4-dimethylaminopyridine as catalyst. Alternative to the esterification in 17 is the use of the carboxylic acid in the presence of dicyclohexylcarbodiimide. Active esters such as trifluoroethyl derivatives or N-acylphthalimide or N-acylbenzotriazoles are further alternatives.

3. The protection in 21 is removed with, for example, tetrakis(triphenylphosphine) Pd and triphenyl phosphine in dichloromethane or tetrahydrofuran to obtain 17α-acyloxy-21-hydroxypregna-4-ene-3,20-dione or 17α-acyloxy-21-hydroxypregna-4,9(11)-diene-3,20-dione.

4. The product from step 3) can subsequently be esterified in 21 with anhydrides of carboxylic acids of 7 carbon atoms or alternatively with the carboxylic acid in the presence of dicyclohexylcarbodiimide, or with active esters such as trifluoroethyl derivatives or N-acylphthalimides or N-acylbenzotriazoles.

EXAMPLE 1

Preparation of 17α,21-dibutanoyloxy-pregna-4,9 (11)-diene-3,20-dione

A mixture of 1 g (2.87 mM) of 17α,21-dihydroxy-pregna-4,9(11)-diene-3,20-dione and of 10 ml of trifluoroethyl butanoate in 50 ml of tetrahydrofuran was reacted at 45° C. in the presence of 5 g of *Candida cylindracea* lipase for 8-10 hours, adding 1 g of lipase at regular time intervals. At the end of this first reaction step, the lipase was filtered off and the filtrate was concentrated under vacuum taking up the residue three times with tetrahydrofuran. The resulting residue was added with further 10 ml of trifluoroethyl butanoate and 50 ml of tetrahydrofuran, the resulting solution was added with 0.8 g of *Bacillus subtilis* protease and the suspension was stirred for 2 days at 45° C., adding further protease at regular time intervals for total 80 mg. The protease was filtered off, the filtrate was removed under vacuum and the residue was chromatographed on a silica gel column with a dichloromethane/methanol 99:1 mixture. The less polar fraction was evaporated to obtain 1 g (2.06 mM) of 17α,21-dibutanoyloxy-pregna-4,9(11)-diene-3,20-dione.

The same procedure was followed, starting from 1 g of 17α,21-dihydroxy-pregna-4-ene-3,20-dione, to obtain 0.98 g (2.01 mM) of 17α,21-dibutanoyloxy-pregna-4-ene-3,20-dione.

EXAMPLE 2

Preparation of 17α-hydroxy-21-butanoyloxy-pregna-4,9(11)-diene-3,20-dione

A mixture of 1 g (2.879 mM) of 17α,21-dihydroxy-pregna-4,9(11)-diene-3,20-dione and 10 ml of trifluoroethyl butanoate in 100 ml of acetone was reacted at 45° C. in the presence of 5 g of *Candida cylindracea* lipase for 8-10 hours, adding 1 g of lipase at regular time intervals. After completion of the reaction, the lipase was filtered off and the filtrate was concentrated under vacuum, taking up the residue three times with acetone. The semi-solid residue was purified by chromatography on a silica gel column with a dichloromethane/methanol 99:1 mixture. The less polar components were removed, to obtain the richer fraction which was evaporated to yield 0.95 g (2.29 mM) of 17α-hydroxy-21-butanoyloxy-pregna-4,9(11)-diene-3,20-dione.

EXAMPLE 3

Preparation of 17α-hydroxy-21-butanoyloxy-pregna-4-ene-3,20-dione

A mixture of 1 g of 17α,21-dihydroxy-pregna-4-ene-3,20-dione and 10 ml of trifluoroethyl butanoate in 50 ml of methyl ethyl ketone was reacted at 45° C. in the presence of 5 g of *Candida cylindracea* lipase for 8-10 hours, adding at regular time intervals 1 g of lipase. After completion of the reaction, the lipase was filtered off, the filtrate was concentrated under vacuum, taking up the residue three times with solvent. The semi-solid residue was purified by chromatography on a silica gel column with a dichloromethane/methanol 99:1 mixture. The richer fraction was evaporated to obtain 0.89 g (2.14 mM) of 17α-hydroxy-21-butanoyloxy-pregna-4-ene-3,20-dione.

EXAMPLE 4

Preparation of 17α-butanoyloxy-21-octadecanoyloxy-pregna-4,9(11)-diene-3,20-dione 4 g (11.6 mM) of 17a,21-dihydroxy-pregna-4,9(11)-diene-3,20-dione were reacted with 20 mg of trifluoroacetic acid in 20 ml of dioxane and 10 ml of ethyl orthobutyrate for 5 hours at 100° C., and the low boiling head fraction was distilled off. The solution was cooled, then treated with 5 ml of a tartaric acid molar solution and heated to 40-50° C. for about 5 minutes to obtain 17α-butanoyloxy-21-hydroxy-pregna-4,9(11)-diene-3,20-dione. The solvent was evaporated off under vacuum and the residue was repeatedly taken up with dioxane. The resulting residue was dissolved in 200 ml of acetone and then 12 g trifluoroethyl octadecanoate (prepared from octadecanoyl chloride and trifluoroethanol), 20 g of *Candida cylindracea* lipase were added and the resulting suspension was stirred for 8-10 hours at 50° C., adding 2 g of *C. cylindracea* at regular time intervals. The lipase was filtered off, the filtrate was concentrated under vacuum and the residue was chromatographed on a silica gel column with a dichloromethane/methanol 98.5:1.5 mixture. The neat fraction was evaporated to obtain 4.9 g (7.17 mM) of 17α-butanoyloxy-21-octadecanoyloxy-pregna-4,9(11)-diene-3,20-dione.

The same procedure was followed, starting from 5 g (14.5 mM) of 17α,21-dihydroxy-pregna-4-ene-3,20-dione, to obtain 5.9 g (8.61 mM) of 17α-butanoyloxy-21-octadecanoyloxy-pregna-4-ene-3,20-dione.

EXAMPLE 5

Preparation of 17α-octadecanoyloxy-21-butanoyloxy-pregna-4,9(11)-diene-3,20-dione Step a: A solution of 2 g of NaOH in 20 ml of water was added with 25 ml of tetrahydrofuran and 5 g (14.5 mM) of 17α,21-dihydroxy-pregna-4,9(11)-diene-3,20-dione. The mixture was stirred at 0° C., then 2.4 ml of allyl chloroformate was dropwise added. After stirring for about 0.5 hours at this temperature, the mixture was carefully neutralized with hydrochloric acid and extracted with dichloromethane. The organic extract was concentrated under vacuum and the residue was subjected to the reaction of the subsequent step.

Step b: Crude 17α-hydroxy-21-allylcarbonyloxy-pregna-4,9(11)-diene-3,20-dione was dissolved in 15 g of trifluoroethyl octadecanoate and 150 ml of tetrahydrofuran, the resulting solution was added with 4 g of *Bacillus subtilis* protease and the suspension was stirred for 2 days at 45° C., adding further protease at regular time intervals to 3 g total. The protease was filtered off, the filtrate was removed under vacuum and the residue was chromatographed on a silica gel column with a dichloromethane/methanol 99:1 mixture. The less polar fraction was evaporated off to obtain a residue of 17α-octadecanoyloxy-21-allylcarbonyloxy-pregna-4,9(11)-diene-3,20-dione.

Step c: the residue from the previous step was dissolved in 50 ml of dichloromethane and added with 35 mg of triphenylphosphine and 35 mg of palladium triphenylphosphine. The resulting mixture was stirred for 0.5 hours at room temperature. The solution was concentrated under vacuum, the residue was taken up twice with dichloromethane, then chromatographed on a silica gel column with a dichloromethane/methanol 99:1 mixture. The richer fraction was evaporated to obtain a neat residue, which was used as such for the subsequent step.

Step d: the residue (6.2 g) of 17α-octadecanoyloxy-21-hydroxy-pregna-4,9(11)-diene-3,20-dione was dissolved in 4 ml butyric anhydride in the presence of 0.5 g of tributylmethylammonium chloride. The mixture was stirred at room temperature for 2 hours, then poured in ice and the resulting product was separated from water by extraction. The extract was washed to neutrality with water and concentrated under vacuum, the residue was crystallized from methanol to obtain 5.5 g (8.05 mM) of 17α-octadecanoyloxy-21-butanoyloxy-pregna-4,9(11)-diene-3,20-dione. This compound was used for the preparation of a pharmaceutical formulation in the form of a cream suitable for cutaneous administration.

The same procedure was followed, starting from 5 g (14.5 mM) of 17α,21-dihydroxy-pregna-4-ene-3,20-dione, to obtain 5.1 g (7.44 mM) of 17α-octadecanoyloxy-21-butanoyloxy-pregna-4-ene-3,20-dione.

The compounds of Examples 1-5 were formulated in suitable formulations, for example in the form of liposome emulsions or suspensions for the transmucosal administration to provide either systemic or topical action, creams, gel and the like.

A typical cream formulation will contain, for example, cetyl alcohol, glycerol monostearate, liquid paraffin, propylene glycol, disodium mono-oleo-amide sulfosuccinate, citric acid monohydrate, purified water.

Using substantially the same methods disclosed in the above examples, the following compounds were prepared:
17α,21-dibutanoyloxy-pregna-4-ene-3,20-dione (mp 101° C., isopropyl ether);
17α-propionyloxy-21-hydroxy-pregna-4-ene-3,20-dione (mp 114° C., isopropyl ether).

EXAMPLE 6

Topical Antiandrogenic Activity (Compound of Example 1)

| Topical treatment | Daily dosage (μg) | Mean difference of the areas (mm$^2$) | % inhibition |
|---|---|---|---|
| Carrier (acetone) | — | 0.0 | — |
| TP | 4 | 22.7 ± 2.3 | — |
| TP + Ex. 1 | 4 + 400 | 3.7 ± 1.1 | 89 |
| DHT | 4 | 20.8 ± 2.5 | — |
| DHT + Ex. 1 | 4 + 400 | 3.7 ± 0.7 | 82 |

EXAMPLE 7

Topical Antiandrogenic Activity (Compound of Example 2)

| Topical treatment | Daily dosage (μg) | Mean difference of the areas (mm$^2$) | % inhibition |
|---|---|---|---|
| Carrier (acetone) | — | 0.0 | — |
| TP | 4 | 22.7 ± 2.3 | — |
| TP + Ex. 2 | 4 + 400 | 3.3 ± 1.2 | 85 |

-continued

| Topical treatment | Daily dosage (µg) | Mean difference of the areas (mm$^2$) | % inhibition |
|---|---|---|---|
| DHT | 4 | 20.8 ± 2.5 | — |
| DHT + Ex. 2 | 4 + 400 | 4.1 ± 0.5 | 80 |

What is claimed is:

1. A pharmaceutical formulation for the treatment of acne, alopecia, hirsutism, or seborrhea, the formulation comprising an effective amount of 17α-propionyloxy-21-hydroxy-pregna-4-ene-3,20-dione, wherein the formulation is suitable for topical application, and wherein the formulation comprises a pharmaceutically acceptable carrier.

2. The pharmaceutical formulation of claim 1, wherein the pharmaceutical formulation is in the form of a cream.

3. The pharmaceutical formulation of claim 1, wherein the pharmaceutical formulation is in the form of a gel.

4. The pharmaceutical formulation of claim 1, wherein the pharmaceutical formulation is in the form of a liposomal emulsion or suspension.

5. The pharmaceutical formulation of claim 2, wherein the cream comprises at least one excipient selected from the group consisting of cetyl alcohol, glycerol monostearate, liquid paraffin, propylene glycol, disodium mono-oleo-amide sulfosuccinate, citric acid monohydrate, and water.

6. The pharmaceutical formulation of claim 5, wherein the cream comprises cetyl alcohol.

7. The pharmaceutical formulation of claim 6, wherein the cream further comprises glycerol monostearate.

8. The pharmaceutical formulation of claim 7, wherein the cream further comprises liquid paraffin.

9. The pharmaceutical formulation of claim 8, wherein the cream further comprises propylene glycol.

10. The pharmaceutical formulation of claim 9, wherein the cream further comprises disodium mono-oleo-amide sulfosuccinate.

11. The pharmaceutical formulation of claim 10, wherein the cream further comprises citric acid monohydrate.

12. The pharmaceutical formulation of claim 11, wherein the cream further comprises water.

13. A method of treating hirsutism, the method comprising administering to a patient in need thereof an effective amount of 17α-propionyloxy-21-hydroxy-pregna-4-ene-3,20-dione.

14. The method of claim 13, wherein the 17α-propionyloxy-21-hydroxy-pregna-4-ene-3,20-dione is applied topically.

15. The method of claim 13, wherein the 17α-propionyloxy-21-hydroxy-pregna-4-ene-3,20-dione is present in a pharmaceutical formulation suitable for topical application.

16. The method of claim 15, wherein the pharmaceutical formulation comprises a pharmaceutically acceptable carrier.

17. The method of claim 15, wherein the pharmaceutical formulation is in the form of a cream.

18. The method of claim 15, wherein the pharmaceutical formulation is in the form of a gel.

19. The method of claim 15, wherein the pharmaceutical formulation is in the form of a liposomal emulsion or suspension.

20. A method of treating seborrhea, the method comprising administering to a patient in need thereof an effective amount of 17α-propionyloxy-21-hydroxy-pregna-4-ene-3,20-dione.

21. The method of claim 20, wherein the 17α-propionyloxy-21-hydroxy-pregna-4-ene-3,20-dione is applied topically.

22. The method of claim 21, wherein the 17α-propionyloxy-21-hydroxy-pregna-4-ene-3,20-dione is present in a pharmaceutical formulation suitable for topical application.

23. The method of claim 22, wherein the pharmaceutical formulation comprises a pharmaceutically acceptable carrier.

24. The method of claim 22, wherein the pharmaceutical formulation is in the form of a cream.

25. The method of claim 22, wherein the pharmaceutical formulation is in the form of a gel.

26. The method of claim 22, wherein the pharmaceutical formulation is in the form of a liposomal emulsion or suspension.

* * * * *